US008708979B2

(12) United States Patent
Honaryar et al.

(10) Patent No.: US 8,708,979 B2
(45) Date of Patent: Apr. 29, 2014

(54) IMPLANTABLE COUPLING DEVICE

(75) Inventors: Babak Honaryar, Orinda, CA (US);
Marcos Borrell, Goleta, CA (US);
Christopher S. Mudd, Goleta, CA (US);
Joseph S. Raven, Goleta, CA (US);
Sean Snow, Capinteria, CA (US); Vern L. Vincent, Santa Barbara, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 712 days.

(21) Appl. No.: 12/904,422

(22) Filed: Oct. 14, 2010

(65) Prior Publication Data

US 2011/0251453 A1    Oct. 13, 2011

Related U.S. Application Data

(63) Continuation-in-part of application No. 12/772,039, filed on Apr. 30, 2010, now Pat. No. 8,506,532.

(60) Provisional application No. 61/237,641, filed on Aug. 27, 2009, provisional application No. 61/236,869, filed on Aug. 26, 2009.

(51) Int. Cl.
*A61M 37/00* (2006.01)

(52) U.S. Cl.
USPC .................................. 604/288.01

(58) Field of Classification Search
USPC ......................... 604/93.01, 288.01
See application file for complete search history.

(56) References Cited

U.S. PATENT DOCUMENTS

| 586,113 A | 7/1897 | Bott |
|---|---|---|
| 2,163,048 A | 6/1939 | McKee |
| 2,737,954 A | 3/1956 | Knapp |
| 3,569,660 A | 3/1971 | Houldcroft |
| 3,587,115 A | 6/1971 | Shiley |
| 3,596,660 A | 8/1971 | Melone |
| 3,667,081 A | 6/1972 | Burger |
| 3,688,764 A | 9/1972 | Reed |
| 3,731,352 A | 5/1973 | Okamoto et al. |
| 3,840,018 A | 10/1974 | Heifetz |
| 3,958,562 A | 5/1976 | Hakim et al. |

(Continued)

FOREIGN PATENT DOCUMENTS

| CN | 1250382 | 4/2000 |
|---|---|---|
| CN | 1367670 | 9/2002 |

(Continued)

OTHER PUBLICATIONS

Helioscopie Product Insert for Heliogast, pp. 1-11 (undated).

(Continued)

*Primary Examiner* — Jason Flick
*Assistant Examiner* — Diva K Chander
(74) *Attorney, Agent, or Firm* — Gordon & Jacobson, PC

(57) ABSTRACT

The present invention provides a system for attaching a fluid access port to a patient. The system generally comprises an implantable access port and method for attaching an access port to a patient. In addition, a tube guard, tube shroud, tissue guard, porous coupling member and a prefabricated mesh member may be attached to the access port. For example, the prefabricated mesh may be coupled to the access port to facilitate securing the access port to the tissue of the patient.

20 Claims, 9 Drawing Sheets

(56) References Cited

U.S. PATENT DOCUMENTS

| | | |
|---|---|---|
| 3,971,376 A | 7/1976 | Wichterle |
| 4,019,499 A | 4/1977 | Fitzgerald |
| 4,118,805 A | 10/1978 | Reimels |
| 4,151,835 A | 5/1979 | Showell et al. |
| 4,161,943 A | 7/1979 | Nogier |
| 4,164,943 A | 8/1979 | Hill et al. |
| 4,190,040 A * | 2/1980 | Schulte ............ 128/899 |
| 4,233,992 A | 11/1980 | Bisping |
| 4,265,252 A | 5/1981 | Chubbuck et al. |
| 4,280,722 A | 7/1981 | Guptil et al. |
| 4,413,985 A | 11/1983 | Wellner |
| 4,474,572 A | 10/1984 | McNaughton et al. |
| 4,502,335 A | 3/1985 | Wamstad et al. |
| 4,543,088 A * | 9/1985 | Bootman et al. ......... 604/288.02 |
| 4,557,722 A | 12/1985 | Harris |
| 4,569,675 A * | 2/1986 | Prosl et al. ............ 604/175 |
| 4,588,394 A | 5/1986 | Schulte et al. |
| 4,592,339 A | 6/1986 | Kuzmak et al. |
| 4,592,355 A | 6/1986 | Antebi |
| 4,634,427 A | 1/1987 | Hannula et al. |
| 4,655,765 A | 4/1987 | Swift |
| 4,673,394 A * | 6/1987 | Fenton et al. ............ 604/175 |
| 4,692,146 A | 9/1987 | Hilger |
| 4,696,288 A | 9/1987 | Kuzmak et al. |
| 4,704,103 A | 11/1987 | Stober et al. |
| 4,710,174 A | 12/1987 | Moden et al. |
| 4,738,657 A | 4/1988 | Hancock et al. |
| 4,767,410 A | 8/1988 | Moden et al. |
| 4,772,270 A | 9/1988 | Wiita et al. |
| 4,778,452 A | 10/1988 | Moden et al. |
| 4,781,680 A | 11/1988 | Redmond et al. |
| 4,796,641 A | 1/1989 | Mills et al. |
| 4,802,885 A | 2/1989 | Weeks et al. |
| 4,832,054 A | 5/1989 | Bark |
| 4,840,615 A * | 6/1989 | Hancock et al. ......... 604/288.02 |
| 4,850,227 A | 7/1989 | Luettgen et al. |
| 4,858,623 A | 8/1989 | Bradshaw et al. |
| 4,861,341 A | 8/1989 | Woodburn |
| 4,881,939 A | 11/1989 | Newman |
| 4,886,501 A * | 12/1989 | Johnston et al. ............ 604/175 |
| 4,898,585 A * | 2/1990 | Borsanyi et al. ............ 604/153 |
| 4,902,278 A | 2/1990 | Maget et al. |
| 4,904,241 A | 2/1990 | Bark |
| 4,913,702 A | 4/1990 | Yum et al. |
| 4,915,690 A | 4/1990 | Cone et al. |
| 4,929,230 A | 5/1990 | Pfleger |
| 4,929,236 A | 5/1990 | Sampson |
| 4,966,588 A | 10/1990 | Rayman et al. |
| 4,967,755 A | 11/1990 | Pohndorf |
| 4,978,338 A | 12/1990 | Melsky et al. |
| 5,006,115 A | 4/1991 | McDonald |
| 5,013,298 A | 5/1991 | Moden et al. |
| 5,026,344 A | 6/1991 | Dijkstra et al. |
| 5,041,098 A | 8/1991 | Loiterman et al. |
| 5,045,060 A | 9/1991 | Melsky et al. |
| 5,074,868 A | 12/1991 | Kuzmak |
| 5,090,954 A | 2/1992 | Geary |
| 5,092,897 A | 3/1992 | Forte |
| 5,094,244 A | 3/1992 | Callahan et al. |
| 5,098,397 A | 3/1992 | Svensson |
| 5,108,377 A | 4/1992 | Cone et al. |
| 5,125,408 A | 6/1992 | Basser |
| 5,133,753 A | 7/1992 | Bark et al. |
| 5,137,529 A | 8/1992 | Watson et al. |
| 5,147,483 A | 9/1992 | Melsky et al. |
| 5,152,747 A | 10/1992 | Olivier |
| 5,167,638 A | 12/1992 | Felix et al. |
| 5,185,003 A | 2/1993 | Brethauer |
| 5,207,644 A | 5/1993 | Strecker |
| 5,213,574 A | 5/1993 | Tucker |
| 5,226,429 A | 7/1993 | Kuzmak |
| 5,226,894 A | 7/1993 | Haber et al. |
| 5,250,026 A | 10/1993 | Ehrlich et al. |
| 5,273,537 A | 12/1993 | Haskvitz et al. |
| 5,281,205 A | 1/1994 | McPherson |
| 5,284,479 A | 2/1994 | de Jong |
| 5,318,545 A | 6/1994 | Tucker |
| 5,336,194 A | 8/1994 | Polaschegg et al. |
| 5,337,747 A | 8/1994 | Neftel |
| 5,360,407 A | 11/1994 | Leonard et al. |
| 5,368,040 A | 11/1994 | Carney |
| 5,387,192 A | 2/1995 | Glantz et al. |
| 5,391,164 A * | 2/1995 | Giampapa ............ 604/891.1 |
| 5,449,368 A | 9/1995 | Kuzmak |
| 5,476,460 A | 12/1995 | Montalvo |
| 5,514,174 A | 5/1996 | Heil, Jr. et al. |
| 5,540,648 A | 7/1996 | Yoon |
| 5,556,388 A | 9/1996 | Johlin, Jr. |
| 5,558,641 A | 9/1996 | Glantz et al. |
| 5,562,617 A | 10/1996 | Finch, Jr. et al. |
| 5,571,104 A | 11/1996 | Li |
| 5,575,777 A | 11/1996 | Cover et al. |
| 5,601,604 A | 2/1997 | Vincent |
| 5,637,102 A | 6/1997 | Tolkoff et al. |
| 5,653,755 A | 8/1997 | Ledergerber |
| 5,658,298 A | 8/1997 | Vincent et al. |
| 5,674,397 A | 10/1997 | Pawlak et al. |
| 5,683,447 A | 11/1997 | Bush et al. |
| 5,688,237 A | 11/1997 | Rozga et al. |
| 5,695,490 A * | 12/1997 | Flaherty et al. ............ 604/891.1 |
| 5,716,342 A | 2/1998 | Dumbraveanu et al. |
| 5,718,682 A | 2/1998 | Tucker |
| 5,722,957 A | 3/1998 | Steinbach |
| 5,748,200 A | 5/1998 | Funahashi |
| 5,810,735 A | 9/1998 | Halperin et al. |
| 5,814,019 A | 9/1998 | Steinbach et al. |
| 5,833,654 A | 11/1998 | Powers et al. |
| 5,843,033 A | 12/1998 | Ropiak |
| RE36,176 E | 3/1999 | Kuzmak |
| 5,883,654 A | 3/1999 | Katsuyama |
| 5,902,598 A | 5/1999 | Chen et al. |
| 5,906,596 A | 5/1999 | Tallarida |
| 5,910,149 A | 6/1999 | Kuzmak |
| 5,911,704 A | 6/1999 | Humes |
| 5,931,829 A | 8/1999 | Burbank et al. |
| 5,932,460 A | 8/1999 | Mills et al. |
| 5,935,083 A | 8/1999 | Williams |
| 5,938,669 A | 8/1999 | Klaiber et al. |
| 5,951,512 A | 9/1999 | Dalton |
| 6,024,704 A | 2/2000 | Meador et al. |
| 6,030,369 A | 2/2000 | Engelson et al. |
| 6,039,712 A | 3/2000 | Fogarty et al. |
| 6,074,341 A | 6/2000 | Anderson et al. |
| 6,090,066 A | 7/2000 | Schnell |
| 6,098,405 A | 8/2000 | Miyata et al. |
| 6,102,678 A | 8/2000 | Peclat |
| 6,102,922 A | 8/2000 | Jakobsson et al. |
| 6,123,700 A | 9/2000 | Mills et al. |
| 6,152,885 A | 11/2000 | Taepke |
| 6,171,252 B1 | 1/2001 | Roberts |
| 6,183,449 B1 | 2/2001 | Sibbitt |
| 6,213,973 B1 | 4/2001 | Eliasen et al. |
| 6,221,024 B1 | 4/2001 | Miesel |
| 6,234,973 B1 | 5/2001 | Meador et al. |
| 6,258,079 B1 | 7/2001 | Burbank et al. |
| 6,264,676 B1 | 7/2001 | Gellman et al. |
| 6,270,475 B1 | 8/2001 | Bestetti |
| 6,283,949 B1 | 9/2001 | Roorda |
| 6,321,124 B1 | 11/2001 | Cigaina |
| 6,349,740 B1 | 2/2002 | Cho et al. |
| 6,432,040 B1 | 8/2002 | Meah |
| 6,450,946 B1 | 9/2002 | Forsell |
| 6,453,907 B1 | 9/2002 | Forsell |
| 6,454,699 B1 | 9/2002 | Forsell |
| 6,459,917 B1 | 10/2002 | Gowda et al. |
| 6,461,293 B1 | 10/2002 | Forsell |
| 6,464,628 B1 | 10/2002 | Forsell |
| 6,470,213 B1 | 10/2002 | Alley |
| 6,470,892 B1 | 10/2002 | Forsell |
| 6,478,783 B1 | 11/2002 | Moorehead |
| 6,511,490 B2 | 1/2003 | Robert |
| 6,547,801 B1 | 4/2003 | Dargent et al. |
| 6,572,587 B2 | 6/2003 | Lerman et al. |
| 6,589,184 B2 | 7/2003 | Noren et al. |

(56) References Cited

U.S. PATENT DOCUMENTS

| | | |
|---|---|---|
| 6,648,849 B2 | 11/2003 | Tenhuisen et al. |
| 6,666,845 B2 | 12/2003 | Hooper et al. |
| 6,689,100 B2 | 2/2004 | Connelly et al. |
| 6,723,053 B2 | 4/2004 | Ackerman et al. |
| 6,733,519 B2 | 5/2004 | Lashinski et al. |
| 6,792,309 B1 | 9/2004 | Noren |
| 6,810,880 B1 | 11/2004 | Jennings, Jr. et al. |
| 6,813,964 B1 | 11/2004 | Clark et al. |
| 6,860,857 B2 | 3/2005 | Noren et al. |
| 6,915,162 B2 | 7/2005 | Noren et al. |
| 6,921,267 B2 | 7/2005 | van Oostrom et al. |
| 6,929,631 B1 | 8/2005 | Brugger et al. |
| 6,939,299 B1 | 9/2005 | Petersen et al. |
| 6,953,444 B2 | 10/2005 | Rosenberg |
| 6,964,204 B2 | 11/2005 | Clark et al. |
| 6,966,875 B1 | 11/2005 | Longobardi |
| 6,997,914 B2 | 2/2006 | Smith et al. |
| 7,017,583 B2 | 3/2006 | Forsell |
| 7,020,531 B1 | 3/2006 | Colliou et al. |
| 7,056,286 B2 | 6/2006 | Ravenscroft et al. |
| 7,063,669 B2 | 6/2006 | Brawner et al. |
| 7,073,387 B2 | 7/2006 | Zdeblick et al. |
| 7,082,843 B2 | 8/2006 | Clark et al. |
| 7,131,945 B2 | 11/2006 | Fink et al. |
| 7,144,400 B2 | 12/2006 | Byrum et al. |
| 7,149,587 B2 | 12/2006 | Wardle et al. |
| 7,191,007 B2 | 3/2007 | Desai et al. |
| 7,195,774 B2 | 3/2007 | Carvalho et al. |
| 7,223,239 B2 | 5/2007 | Schulze |
| 7,226,419 B2 | 6/2007 | Lane et al. |
| 7,261,003 B2 | 8/2007 | McDonald et al. |
| 7,267,645 B2 | 9/2007 | Anderson et al. |
| 7,282,023 B2 | 10/2007 | Frering |
| 7,311,716 B2 | 12/2007 | Byrum |
| 7,311,717 B2 | 12/2007 | Egle |
| 7,351,198 B2 | 4/2008 | Byrum et al. |
| 7,351,226 B1 | 4/2008 | Herskowitz |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,367,937 B2 | 5/2008 | Jambor et al. |
| 7,374,557 B2 | 5/2008 | Conlon |
| 7,374,565 B2 | 5/2008 | Hassler, Jr. et al. |
| 7,390,294 B2 | 6/2008 | Hassler, Jr. |
| 7,413,547 B1 | 8/2008 | Lichtscheidl et al. |
| 7,416,528 B2 | 8/2008 | Crawford et al. |
| 7,437,951 B2 | 10/2008 | McDonald et al. |
| 7,438,718 B2 | 10/2008 | Milliman et al. |
| 7,445,614 B2 | 11/2008 | Bunodiere et al. |
| 7,468,038 B2 | 12/2008 | Ye et al. |
| 7,500,944 B2 | 3/2009 | Byrum et al. |
| 7,510,530 B2 | 3/2009 | Hashimoto et al. |
| 7,513,892 B1 * | 4/2009 | Haarala et al. ............ 604/288.02 |
| 7,530,943 B2 | 5/2009 | Lechner |
| 7,553,298 B2 | 6/2009 | Hunt |
| 7,561,916 B2 | 7/2009 | Hunt |
| 7,580,746 B2 | 8/2009 | Gilkerson et al. |
| 7,591,185 B1 | 9/2009 | Mothilal et al. |
| 7,593,777 B2 | 9/2009 | Gerber |
| 7,634,319 B2 | 12/2009 | Schneider et al. |
| 7,651,483 B2 | 1/2010 | Byrum |
| 7,658,196 B2 | 2/2010 | Ferreri et al. |
| 7,699,770 B2 | 4/2010 | Hassler, Jr. et al. |
| 7,708,722 B2 | 5/2010 | Glenn |
| 7,762,998 B2 | 7/2010 | Birk et al. |
| 7,762,999 B2 | 7/2010 | Byrum |
| 7,775,215 B2 | 8/2010 | Hassler, Jr. et al. |
| 7,775,966 B2 | 8/2010 | Dlugos et al. |
| 7,811,275 B2 * | 10/2010 | Birk et al. ..................... 604/502 |
| 7,850,660 B2 | 12/2010 | Uth et al. |
| 7,862,546 B2 | 1/2011 | Conlon et al. |
| 7,901,381 B2 * | 3/2011 | Birk et al. ..................... 604/175 |
| 7,909,754 B2 | 3/2011 | Hassler, Jr. et al. |
| 7,909,804 B2 * | 3/2011 | Stats ........................ 604/288.01 |
| 7,972,315 B2 * | 7/2011 | Birk et al. ................ 604/288.01 |
| 8,007,474 B2 | 8/2011 | Uth et al. |
| 8,079,989 B2 * | 12/2011 | Birk et al. ................ 604/288.01 |
| 8,231,609 B2 * | 7/2012 | Pang et al. .................. 604/891.1 |
| 8,366,687 B2 * | 2/2013 | Girard et al. ............. 604/288.02 |
| 2001/0052141 A1 | 12/2001 | Andersen |
| 2002/0013545 A1 | 1/2002 | Soltanpour et al. |
| 2002/0058969 A1 | 5/2002 | Noren et al. |
| 2002/0087147 A1 | 7/2002 | Hooper et al. |
| 2002/0095181 A1 | 7/2002 | Beyar |
| 2002/0139208 A1 | 10/2002 | Yatskov |
| 2002/0198548 A1 | 12/2002 | Robert |
| 2003/0045800 A1 | 3/2003 | Noren et al. |
| 2003/0045910 A1 | 3/2003 | Sorensen et al. |
| 2003/0073880 A1 | 4/2003 | Polsky et al. |
| 2003/0078506 A1 | 4/2003 | Noren et al. |
| 2003/0139690 A1 | 7/2003 | Aebli et al. |
| 2004/0064110 A1 | 4/2004 | Forsell |
| 2004/0065615 A1 | 4/2004 | Hooper et al. |
| 2004/0068233 A1 | 4/2004 | DiMatteo |
| 2004/0082908 A1 | 4/2004 | Whitehurst et al. |
| 2004/0111050 A1 | 6/2004 | Smedley et al. |
| 2004/0204692 A1 | 10/2004 | Eliasen |
| 2004/0254536 A1 | 12/2004 | Conlon et al. |
| 2004/0254537 A1 | 12/2004 | Conlon |
| 2004/0260229 A1 | 12/2004 | Meir |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0010177 A1 | 1/2005 | Tsai |
| 2005/0049578 A1 | 3/2005 | Tu et al. |
| 2005/0070875 A1 | 3/2005 | Kulessa |
| 2005/0070937 A1 | 3/2005 | Jambor et al. |
| 2005/0085778 A1 | 4/2005 | Parks |
| 2005/0092093 A1 | 5/2005 | Kang et al. |
| 2005/0131325 A1 | 6/2005 | Chen et al. |
| 2005/0131352 A1 | 6/2005 | Conlon |
| 2005/0131383 A1 | 6/2005 | Chen et al. |
| 2005/0148956 A1 | 7/2005 | Conlon |
| 2005/0149143 A1 | 7/2005 | Libbus et al. |
| 2005/0209573 A1 | 9/2005 | Brugger et al. |
| 2005/0240155 A1 | 10/2005 | Conlon |
| 2005/0240156 A1 | 10/2005 | Conlon |
| 2005/0267500 A1 | 12/2005 | Hassler, Jr. et al. |
| 2005/0277899 A1 | 12/2005 | Conlon |
| 2005/0283041 A1 | 12/2005 | Egle |
| 2005/0283118 A1 | 12/2005 | Uth |
| 2005/0283119 A1 | 12/2005 | Uth |
| 2006/0074439 A1 | 4/2006 | Garner et al. |
| 2006/0122578 A1 | 6/2006 | Lord et al. |
| 2006/0161186 A1 | 7/2006 | Hassler, Jr. et al. |
| 2006/0173423 A1 | 8/2006 | Conlon |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0189887 A1 | 8/2006 | Hassler, Jr. et al. |
| 2006/0189888 A1 | 8/2006 | Hassler, Jr. et al. |
| 2006/0190039 A1 | 8/2006 | Birk |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0217668 A1 | 9/2006 | Schulze et al. |
| 2006/0217673 A1 * | 9/2006 | Schulze et al. ........... 604/288.02 |
| 2006/0235445 A1 | 10/2006 | Birk |
| 2006/0235448 A1 | 10/2006 | Roslin et al. |
| 2006/0247539 A1 | 11/2006 | Schugt et al. |
| 2006/0266128 A1 | 11/2006 | Clark et al. |
| 2006/0293625 A1 | 12/2006 | Hunt et al. |
| 2006/0293626 A1 | 12/2006 | Byrum et al. |
| 2006/0293627 A1 | 12/2006 | Byrum |
| 2006/0293628 A1 | 12/2006 | Hunt et al. |
| 2007/0010790 A1 | 1/2007 | Byrum et al. |
| 2007/0015954 A1 | 1/2007 | Dlugos |
| 2007/0015955 A1 | 1/2007 | Tsonton |
| 2007/0016231 A1 | 1/2007 | Jambor et al. |

(56) References Cited

U.S. PATENT DOCUMENTS

| | | |
|---|---|---|
| 2007/0027356 A1 | 2/2007 | Ortiz |
| 2007/0038255 A1 | 2/2007 | Kieval et al. |
| 2007/0060959 A1 | 3/2007 | Salo et al. |
| 2007/0073250 A1 | 3/2007 | Schneiter |
| 2007/0078391 A1 | 4/2007 | Wortley |
| 2007/0088336 A1 | 4/2007 | Dalton |
| 2007/0088391 A1 | 4/2007 | McAlexander |
| 2007/0129765 A1 | 6/2007 | Gilkerson et al. |
| 2007/0135758 A1 | 6/2007 | Childers et al. |
| 2007/0149947 A1 | 6/2007 | Byrum |
| 2007/0156013 A1 | 7/2007 | Birk |
| 2007/0158769 A1 | 7/2007 | You |
| 2007/0161958 A1 | 7/2007 | Glenn |
| 2007/0167672 A1 | 7/2007 | Dlugos et al. |
| 2007/0173685 A1 | 7/2007 | Jambor et al. |
| 2007/0185462 A1 | 8/2007 | Byrum |
| 2007/0191717 A1 | 8/2007 | Rosen et al. |
| 2007/0205384 A1 | 9/2007 | Kurosawa |
| 2007/0208313 A1 | 9/2007 | Conlon |
| 2007/0213837 A1 | 9/2007 | Ferreri et al. |
| 2007/0219510 A1 | 9/2007 | Zinn et al. |
| 2007/0235083 A1 | 10/2007 | Dlugos |
| 2007/0250086 A1 | 10/2007 | Wiley et al. |
| 2007/0255165 A1 | 11/2007 | Uesugi et al. |
| 2007/0255234 A1 | 11/2007 | Haase et al. |
| 2007/0265666 A1 | 11/2007 | Roberts et al. |
| 2007/0282196 A1 | 12/2007 | Birk et al. |
| 2007/0293829 A1 | 12/2007 | Conlon et al. |
| 2008/0009680 A1 | 1/2008 | Hassler, Jr. |
| 2008/0015406 A1 | 1/2008 | Dlugos et al. |
| 2008/0039772 A1 | 2/2008 | Chantriaux et al. |
| 2008/0058632 A1 | 3/2008 | Tai et al. |
| 2008/0097496 A1 | 4/2008 | Chang et al. |
| 2008/0114308 A1 | 5/2008 | di Palma et al. |
| 2008/0119798 A1 | 5/2008 | Chantriaux et al. |
| 2008/0243093 A1 | 10/2008 | Kalpin et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0281412 A1 | 11/2008 | Smith et al. |
| 2008/0287969 A1 | 11/2008 | Tsonton et al. |
| 2008/0287974 A1 | 11/2008 | Widenhouse et al. |
| 2008/0312553 A1 | 12/2008 | Timmons |
| 2008/0319435 A1 | 12/2008 | Rioux et al. |
| 2009/0018608 A1 | 1/2009 | Schwartz et al. |
| 2009/0048524 A1 | 2/2009 | Wildau et al. |
| 2009/0054914 A1 | 2/2009 | Lechner |
| 2009/0062825 A1 | 3/2009 | Pool et al. |
| 2009/0071258 A1 | 3/2009 | Kouda et al. |
| 2009/0076466 A1 | 3/2009 | Quebbemann et al. |
| 2009/0082757 A1 | 3/2009 | Rogers et al. |
| 2009/0082793 A1 | 3/2009 | Birk |
| 2009/0093768 A1 | 4/2009 | Conlon et al. |
| 2009/0099538 A1 | 4/2009 | Paganon |
| 2009/0105735 A1 | 4/2009 | Stam et al. |
| 2009/0112308 A1 | 4/2009 | Kassem |
| 2009/0118572 A1 | 5/2009 | Lechner |
| 2009/0149874 A1 | 6/2009 | Ortiz et al. |
| 2009/0157106 A1 | 6/2009 | Marcotte |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0221974 A1 | 9/2009 | Paganon |
| 2009/0222031 A1 | 9/2009 | Axelsson |
| 2009/0222065 A1 | 9/2009 | Dlugos, Jr. et al. |
| 2009/0227862 A1 | 9/2009 | Smith et al. |
| 2009/0228028 A1 | 9/2009 | Coe |
| 2009/0228072 A1 | 9/2009 | Coe et al. |
| 2009/0248125 A1 | 10/2009 | Brostrom |
| 2009/0248126 A1 | 10/2009 | Nippoldt et al. |
| 2009/0254052 A1 | 10/2009 | Birk et al. |
| 2009/0259190 A1 | 10/2009 | Birk et al. |
| 2009/0259191 A1 | 10/2009 | Birk et al. |
| 2009/0259231 A1 | 10/2009 | Birk et al. |
| 2009/0264901 A1 | 10/2009 | Franklin |
| 2009/0270904 A1 | 10/2009 | Birk et al. |
| 2009/0299216 A1 | 12/2009 | Chen et al. |
| 2009/0299672 A1 | 12/2009 | Zhang et al. |
| 2009/0306462 A1 | 12/2009 | Lechner |
| 2009/0308169 A1 | 12/2009 | Mothilal et al. |
| 2010/0087843 A1 | 4/2010 | Bertolote et al. |
| 2010/0100079 A1 | 4/2010 | Berkcan et al. |
| 2010/0114149 A1 | 5/2010 | Albrecht et al. |
| 2010/0130941 A1 | 5/2010 | Conlon et al. |
| 2010/0152532 A1 | 6/2010 | Marcotte |
| 2010/0191271 A1 | 7/2010 | Lau et al. |
| 2010/0211085 A1 | 8/2010 | Uth et al. |
| 2010/0217198 A1 | 8/2010 | Franklin et al. |
| 2010/0217199 A1 | 8/2010 | Uth et al. |
| 2010/0217200 A1 | 8/2010 | Uth et al. |
| 2010/0228080 A1 | 9/2010 | Tavori et al. |
| 2010/0234808 A1 | 9/2010 | Uth et al. |
| 2011/0054407 A1 | 3/2011 | Olroyd et al. |
| 2011/0082426 A1 | 4/2011 | Conlon et al. |

FOREIGN PATENT DOCUMENTS

| | | |
|---|---|---|
| DE | 3927001 | 2/1991 |
| DE | 4211045 | 10/1993 |
| DE | 19751791 | 5/1997 |
| DE | 19745654 | 4/1999 |
| EP | 0343910 | 11/1989 |
| EP | 0611561 | 9/1993 |
| EP | 0858814 | 8/1998 |
| EP | 0867197 | 9/1998 |
| EP | 1057457 | 12/2000 |
| EP | 1346753 | 9/2003 |
| EP | 1396242 | 3/2004 |
| EP | 1396243 | 3/2004 |
| EP | 1488824 | 12/2004 |
| EP | 1543861 | 6/2005 |
| EP | 1547643 | 6/2005 |
| EP | 1591140 | 11/2005 |
| EP | 1736194 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 | 6/2009 |
| EP | 2095798 | 9/2009 |
| FR | 2740977 | 5/1997 |
| FR | 2797181 | 2/2001 |
| FR | 2823663 | 10/2002 |
| FR | 2851168 | 8/2004 |
| FR | 2855744 | 12/2004 |
| FR | 2916980 | 12/2008 |
| JP | 2119877 | 5/1990 |
| JP | 8107934 | 4/1996 |
| SU | 1823791 | 6/1991 |
| WO | WO 92/20519 | 11/1992 |
| WO | WO 94/22520 | 10/1994 |
| WO | WO 96/40357 | 12/1996 |
| WO | WO 97/01370 | 1/1997 |

(56) References Cited

FOREIGN PATENT DOCUMENTS

| WO | WO 99/20338 | 4/1999 |
|---|---|---|
| WO | WO 99/26543 | 6/1999 |
| WO | WO 99/34859 | 7/1999 |
| WO | WO 00/15158 | 3/2000 |
| WO | WO 00/33901 | 6/2000 |
| WO | WO 01/10359 | 2/2001 |
| WO | WO 01/49245 | 7/2001 |
| WO | WO 01/080926 | 11/2001 |
| WO | WO 01/95813 | 12/2001 |
| WO | WO 02/10667 | 2/2002 |
| WO | WO 02/074381 | 9/2002 |
| WO | WO 03/105732 | 12/2003 |
| WO | WO 2004/016971 | 3/2004 |
| WO | WO 2005/037055 | 4/2005 |
| WO | WO 2005/072627 | 8/2005 |
| WO | WO 2006/021695 | 3/2006 |
| WO | WO 2009/007526 | 1/2009 |
| WO | WO 2009/129474 | 10/2009 |

OTHER PUBLICATIONS

Autumn K. et al.; "Evidence of Van Der Waals Adhesion in Gecko Setae"; PNAS; vol. 99; No. 19; pp. 12252-12256; Sep. 17, 2012.
Geim AK. et al.; "Microfabricated Adhesive Mimicking Gecko Foot-Hair"; Nature Materials Abstract only; vol. 2; No. 7; 2003.
Yamagami, Takuji; "Technical Developments: Use of Targeting Guide Wire in Left Subclavian Puncture During Percutaneous Implantation of Port-Catheter Systems Using the Catheter Tip Fixation Method" European Radiology; vol. 13; pp. 863-866; 2003.
Yurdumakan B., et al.; "Synthetic Gecko Foot-Hairs from Multiwalled Carbon Nanotubes"; The Royal Society of Chemistry; p. 3799-3801; 2005.
http://en/wikipedia.org/Injection_Molding.

* cited by examiner

IMPLANTABLE COUPLING DEVICE

RELATED APPLICATIONS

This application is a continuation in part of, and claims priority to and the benefit of U.S. patent application Ser. No. 12/772,039, entitled "SYSTEM INCLUDING ACCESS PORT AND APPLICATOR TOOL" filed on Apr. 30, 2010, which claims priority to and the benefit of U.S. Provisional Patent Application No. 61/237,641, filed on Aug. 27, 2009, and U.S. Provisional Patent Application No. 61/236,869, filed on Aug. 26, 2009, all of these applications are hereby expressly incorporated by reference herein.

FIELD

The present invention generally relates to medical systems and apparatus and uses thereof for treating obesity or obesity-related diseases, and more specifically, relates to access ports and methods for applying the same to bodily tissue.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts food's passage into a lower portion of the stomach. When the stoma is of an appropriate size that is restricted by a gastric band, food held in the upper portion of the stomach may provide a feeling of satiety or fullness that discourages overeating. Unlike gastric bypass procedures, gastric band apparatus are reversible and require no permanent modification to the gastrointestinal tract.

Medical implants, including gastric band systems, for performing therapeutic functions for a patient are well known. Such devices include pace makers, vascular access ports, injection ports (such as used with gastric banding systems) and gastric pacing devices. Such implants need to be attached, typically subcutaneously, in an appropriate place in order to function properly.

Many implantable medical devices are secured with sutures. For example, when inserting a gastric band and an associated access port, the associated access port may be sutured into place with sutures against the rectus muscle sheath. Such placement of the sutures is often challenging because the associated access port is placed below several inches of bodily tissue (e.g., fat), and suturing the associated access port often takes as long as placing the gastric band itself.

Additionally, the sutures can cause post surgical pain for the patient due to the inherent pulling and slight tearing of the tissue pieces by and adjacent to the suture.

Also, it is common for medical professionals desiring to add or remove fluid via a needle through the access port to palpitate the skin to locate the implanted port. The medical professional has a general idea of the top surface of the port, but occasionally will accidentally miss the septum and puncture the tube and/or tissue surrounding or adjacent to the port.

Further, some body-related systems utilize retention geometry for the access port attachment such as Bestetti, et al., U.S. Pat. No. 6,270,475. However, Bestetti discloses a percutaneous access port not a subcutaneous access port. Similarly, Svensson, et al., U.S. Pat. No. 5,098,397, discloses a percutaneous access port not a subcutaneous access port.

Conlon, et al., U.S. Pat. No. 7,374,557, generally discloses self attaching injection ports comprising integral fasteners for subcutaneous attachment. However, Conlon does not disclose a tube guard, a tissue guard, or a porous coupling device.

U.S. Patent Publication Nos. 2005/0131352 and 2004/0254537 to Conlon, et al., also generally disclose a self attaching injection port comprising integral fasteners for subcutaneous attachment. Patent Publication Nos. 2005/0131352 and 2004/0254537 do not disclose a tube guard, a tissue guard, or a porous coupling device.

Accordingly, there remains a need for a procedure to implant medical devices in a quick, easy and efficient manner, utilizing as small of an incision as possible which reduces the likelihood of future discomfort for the patient.

SUMMARY

The present invention, in one embodiment, provides an implantable coupling device configured to facilitate coupling an implantable access port to a tissue of a patient. The device may include a porous coupling member having a top surface and a bottom surface and a coupling agent proximate the top surface of the porous coupling member for mating with a base of the implantable access port of an adjustable gastric banding system. The porous coupling member may extend substantially parallel to the base of the implantable access port. The bottom surface of the porous coupling member may be configured for anchoring the porous coupling member to the tissue of the patient. The access port may be latched onto an interior portion, or muscle portion of a patient through various methods described herein.

In one embodiment, the porous coupling member is made from an injection moldable plastic or rubber material. In another embodiment, the porous coupling member is overmolded on at least one of a fabric or woven mesh material. The porous coupling member may include at least one flexible flange.

The porous coupling member may comprise a tissue shield such as a first portion extending substantially parallel to the base of the implantable access port which does not comprise a porous surface and a second portion extending substantially parallel to the base of the implantable access port which comprises a porous surface. The first portion may be proximate to the implantable access port.

In one embodiment, the porous coupling member includes a raised canopy configured to permit the passage of a tube coupled to a side surface of the implantable access port. The surface of the raised canopy may be configured to shield the tube from contact with a needle. A surface of the raised canopy may be formed to mirror a portion of the side surface of the implantable access port. The device may include a hingeable shroud extending distally from the canopy or port.

In one embodiment the raised canopy is hingably coupled to or integral to the porous coupling member. The porous coupling member may include a notch under the canopy configured to permit the flexing of the tube without interference with the implantable coupling device.

In another embodiment, an implantable coupling device includes a coupling member having a top surface and a bottom surface and a pre-fabricated mesh material with at least one through hole configured to allow the passage of a coupler.

The top surface of the coupling member includes at least one coupler for mating with the base of an implantable access port of an adjustable gastric banding apparatus. The pre-fabricated mesh material may be sandwichably oriented between the implantable access port and the coupling member. In one embodiment, the pre-fabricated mesh material is made from an injection moldable plastic or rubber material.

The pre-fabricated mesh material may include a notch under the canopy configured to permit the flexing of the tube below the plane of a bottom surface of the pre-fabricated mesh material without interference with the pre-fabricated mesh material. In one embodiment, the device includes a hingeable shroud extending distally from the canopy. The coupling member and/or pre-fabricated mesh material further comprises a flange configured to flex with the movement of the tissue of the patient. The coupler may be at least one of a partial ring shape or a substantially circular shape.

In various embodiments, an implantable coupling device, configured to facilitate coupling an implantable access port to a tissue of a patient, includes a coupling member having a top surface and a bottom surface. The coupling member may include a raised canopy configured to permit the passage of a tube coupled to a side surface of the implantable access port, and the coupling member may be configured for anchoring the coupling member to a tissue of a patient. The coupling member may include a coupling agent proximate to the top surface of the porous coupling member for mating with a base of the implantable access port of an adjustable gastric banding system.

In one embodiment, an implantable anchoring device includes a first anchoring member and a second anchoring member. The first anchoring member and second anchoring members may have a first top surface and a first bottom surface. A first beam of the first anchoring member may be configured to extend through a first opening in a second anchoring member in response to the first anchoring member being rotated about an axis from a first position to a second position. A second beam of the second anchoring member may be configured to release through a second opening in the first anchoring member in response to the first anchoring member being rotated about the axis from the first position to the second position. The second top surface of the second anchoring member may be configured to attachably mate with a base of an implantable access port housing of an adjustable gastric banding system. The first beam may be integral to the first anchoring member and the second beam may be integral to the second anchoring member. The first beam and the second beam may be configured to return to a preset deployed position in response to the first anchoring member being moved from the first position into the second position.

These and other aspects of the invention may be more clearly understood or appreciated by referring to the accompanying drawings and the detailed description.

DETAILED DESCRIPTION

The present invention relates to implantable medical devices and fasteners therefore and more specifically to access ports and methods for applying the same to bodily tissue. Specifically, the present invention is directed to a subcutaneous implantable gastric banding system including an access port coupled to bodily tissue. In some embodiments, a tube guard, a tube hingeable shroud, and/or a tissue guard may reduce pain caused by errant needle sticks/strikes or follow-up surgery needed to repair damaged components.

In various embodiments, the present invention utilizes tube guards, hingeable tube shrouds, tissue shields, pre-fabricated mesh and porous coupling devices and/or combinations thereof to protect the patient from unnecessary pain or discomfort. In some embodiments, a mesh material (described in greater detail below) may be used to anchor an access port to a patient's tissue. For example, the mesh material may encourage tissue ingrowth or tissue engagement through holes and spaces of the mesh material. This use of mesh materials to anchor the access port using the patient's own tissue engagement may obviate the need for sutures during implantation. For example, where access port implantation may occur using sutures, during recovery and beyond, movement of the patient may cause discomfort due to a pulling and slight tearing of the tissue around the implantation site. Use of a porous coupling device or prefabricated mesh material according to embodiments of the present invention may eliminate or substantially reduce this discomfort.

Figure 1:
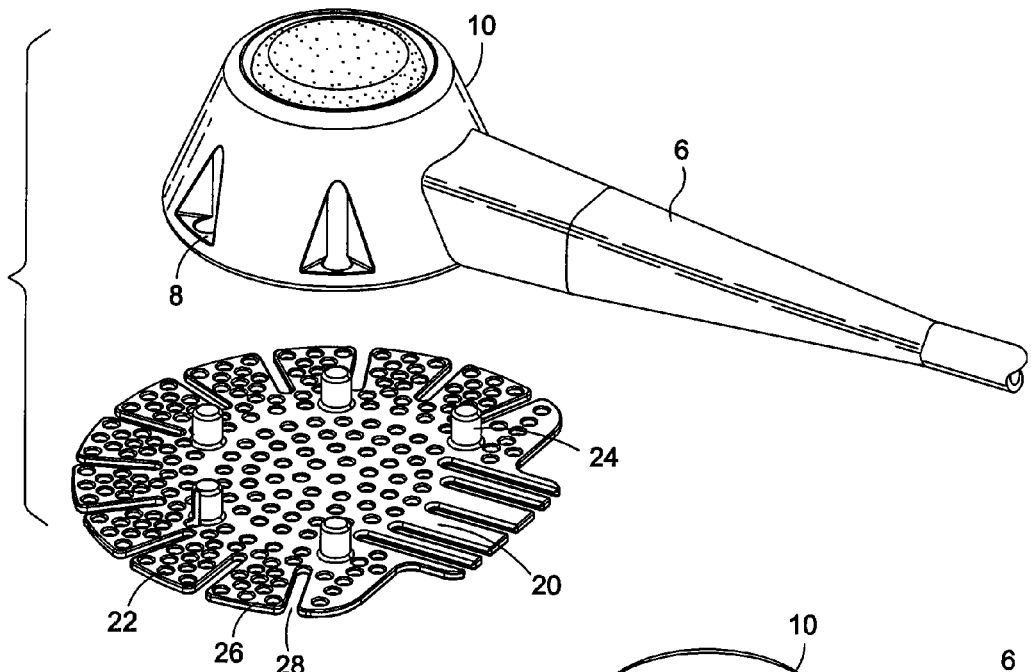
FIG. 1 illustrates a gastric band port and a coupling device according to an embodiment of the present invention.

In accordance with various embodiments, FIG. 1 illustrates a simplified perspective view of an access port 10 for use in conjunction with an implantable medical device, such as an implantable gastric banding system. The access port 10 may comprise a septum 15 for passing fluid into the access port 10, or removing fluid by means of the access port 10, via a needle. The access port 10 may provide a convenient means for inflating and/or deflating a conventional gastric band, thereby enabling adjustment of a size of a stoma or a level of restriction on a patient's stomach. A tube 6, coupled to or integral to the access port 10, passes the fluid from the access port 10 to and from the gastric band. The access port 10 is generally fixed within the interior of a patient's body, preferably secured to a patient's abdominal muscle.

In various embodiments, the access port 10 comprises at least one anchoring surface 8. The anchoring surface 8 may comprise any suitable anchoring surface, such as a latch, clip, hole, ridge, surface deformity, notch, flange and/or the like. The anchoring surface 8 comprises a plurality of through holes, such as suture holes. The housing of the access port 10 may comprise any suitable geometry, such as conical, cylindrical, square, block, and/or the like. The side wall of the housing of the access port 10 may comprise a surface transition to assist the operation of the anchoring surface 8. For example, the side wall of the tapered access port 10 comprises notches to assist material being threaded through the opening of the anchoring surface 8.

With continued reference to FIG. 1, and in accordance with various embodiments, a coupler 20 for assisting with the anchoring of the port 10 is depicted. The coupler 20 may comprise any suitable geometry. In one embodiment, the perimeter of the coupler 20 is larger than and extends away from the port 10 in a plane parallel to the bottom surface of the base of the port 10. The portion of the coupler 20 extending beyond the base may extend outwardly from and substantially circumscribe the base, or may extend only partially around the base of the port 10. The coupler 20 comprises a top surface and a bottom surface. The side surface of the coupler 20 may be any suitable shape such as curved or straight with any suitable thickness. The top surface of the coupler 20 comprises coupling agents 24 configured to attach the coupler 20 to the base of the port 10. These coupling agents 24 may be any suitable material and shape. For example, these coupling agents 24 may be glue, epoxy, welds, such as ultrasonic welding, posts, knobs, bolts, screws, barbs, clamps, clips and/or the like, and combinations thereof.

In one embodiment, as illustrated in FIG. 1, the coupling agent 24 comprises one or more posts configured to create an interference fit with an opening of the anchoring surface 8 of the port 10. This interference fit may be a press fit, a friction fit, or a push fit. The location of the coupling agents 24 may be pre-selected based upon the preexisting locations of suture holes on the port 10. In one embodiment, the coupling agent 24 may be configured to latch onto the previously described surface transition of a side wall of the port 10 housing (not depicted).

Further, in an embodiment, a portion of the coupler 20 may be porous. For instance, a plurality of though holes 22 may pass from the top surface to the bottom surface of the coupler 20. These though holes 22 may be configured to allow for tissue ingrowth or tissue engagement through the though holes 22 to serve as or assist with the anchoring of the port 10 with the patient. The though holes 22 may be formed in any configuration. For example, the spacing of the holes may be regular or irregular. The though holes 22 may be formed in substantially the entire surface of the coupler 20 or the though holes 22 may be located in a particular portion(s) of the coupler 20. For example, the though holes 22 may be located towards the outer perimeter of the coupler 20 leaving a portion of the surface without though holes 22 proximate the base of the port 10.

In one embodiment, the coupler 20 may comprise one or more flanges 26 configured to support the flexing of the anchoring surface of the patient, such as the patient's abdominal wall adjacent to and coupled to the bottom surface of the coupler 20. For example, with reference to FIG. 1, the flange 26 may be formed by forming a groove 28 in the coupler 20. The coupler 20 may be made from any suitable material. For example, the coupler 20 may be made from an injection molded plastic material, injection molded rubber material, compression molded material, transfer molded material, over-molded plastic over mesh, and/or the like. In one embodiment, the coupler 20 may be integral to a surface, such as the bottom surface of the port 10.

Figure 2B:
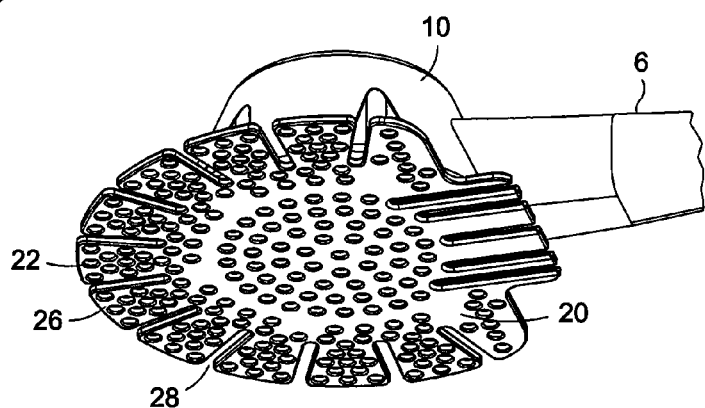
FIG. 2B illustrates a perspective bottom view of a mated port and the coupling device of FIG. 2A according to an embodiment of the present invention.
Figure 2A:
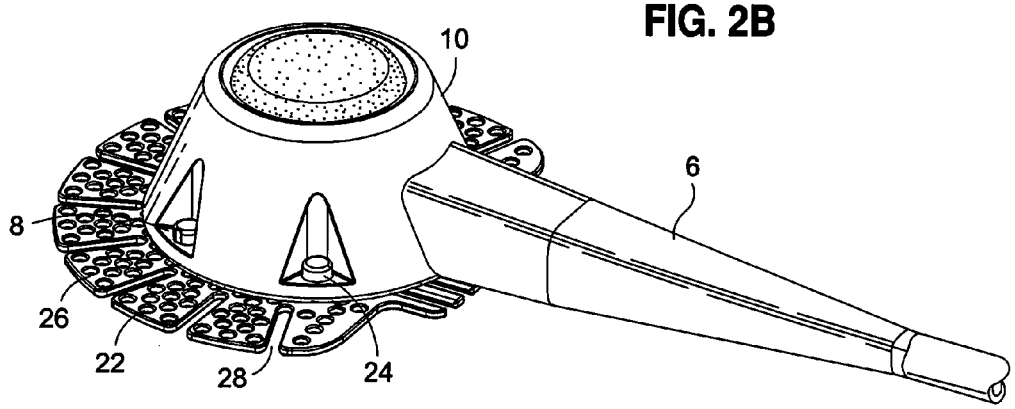
FIG. 2A illustrates a perspective view of an implantable access port and a coupling device mated together according to an embodiment of the present invention.

Turning now to FIG. 2A, in accordance with an embodiment, the top surface of the coupler 20 is depicted as being mated with the bottom surface of the port 10 as illustrated in FIG. 1. At least a portion of the coupler 20 extends beyond the bottom surface of the port 10. The coupling agents 24 are sized to create an inference fit with the anchoring surface 8 of the port 10 to facilitate connecting the coupler 20 to the port 10.

With reference to FIG. 2B, according to an embodiment, a portion of the through holes 22 allows tissue growth up through the through holes 22 and above the top surface of the coupler 20. A portion of the through holes 22 allows tissue growth up through the through holes 22 to the bottom surface of the port 10. In one embodiment, a spacer disposed between, on, near, or integral to the coupling agents 24 creates a gap between the coupler 20 and the bottom surface of the port 10 to allow tissue growth through substantially one or more through holes 22.

In this manner, the body's own tissue may grow into coupler 20 and act as an anchoring mechanism. This anchoring may be more comfortable for the patient post surgery than previous access port anchoring methods and techniques.

Figure 3A:
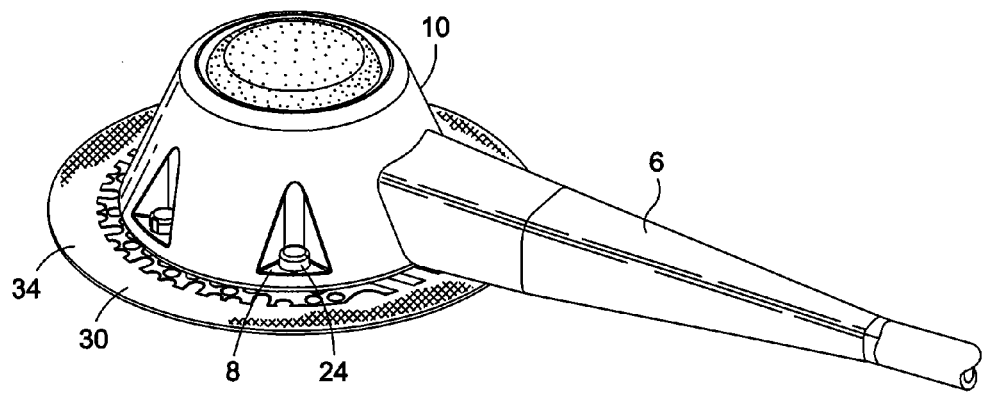
FIG. 3A illustrates a perspective view of a port mated with an over-molded coupling device according to an embodiment of the present invention.

Turning now to FIG. 3A, according to various embodiments, a coupler 30 formed, from an attachment material such as a mesh member 34 over-molded with an injection molded plastic or rubber material is illustrated. The coupler 30 and the mesh member 34 may be configured to encourage tissue ingrowth or tissue engagement after the access port 10 has been implanted in the patient. Stated another way, the mesh material is molded onto a biocompatible material such as injection molded plastic or a rubber coupler having the coupling agents 24. The mesh member 34 may have a generally web-shape or checkerboard shape, including a plurality of structures that cross in varied directions to form a series of intersections and spaces (for example, as shown, according to various embodiments, in FIGS. 4 and 5). In addition, the mesh member 34 may have a microstructure much smaller than shown in the Figures, or may have a circular, triangular, or other equivalent mesh structure. In one embodiment, the mesh member 34 may comprise a porous material. The outer parameter of the mesh member 34 may comprise any suitable shape, such as square, rectangular, free form, or circular shape.

The mesh member 34 may encourage local tissue growth around the access port 10 to engage with the access port 10 after the access port 10 has been applied. The mesh member 34 aids in securing the access port 10 in place on the patient's tissue. In addition, the mesh member 34 may aid in forming a biological seal, or a dermal interface, around the interface between the tissue and the access port 10. In addition, the mesh member 34 may prevent the local tissue from rejecting the access port 10 and may decrease the chance of medical complications related to the access port 10.

Furthermore, a portion of the mesh member 34 may be used as an attachment point to suture, staple, tack or otherwise fasten the access port 10 to the patient's body.

In various embodiments, the mesh member 34 may be made of a bioresorbable material, such as silk, or the like, or may be made of a non-resorbable material such as polypropylene, or the like. In addition, the mesh member 34 may be made of a blend of both bioresorbable materials and non-resorbable materials such as a Covidien mesh, or the like.

The mesh member 34 may include apertures appropriately sized to allow a portion of the coupling agents 24 to pass through the mesh member 34. In addition, the mesh member 34 may be sized and spaced to allow the coupling agents 24 to pass through the mesh member 34 without contacting or damaging the mesh member 34. In one embodiment, the mesh member 34 and sutures may be used to engage the bodily tissue.

Figure 3B:
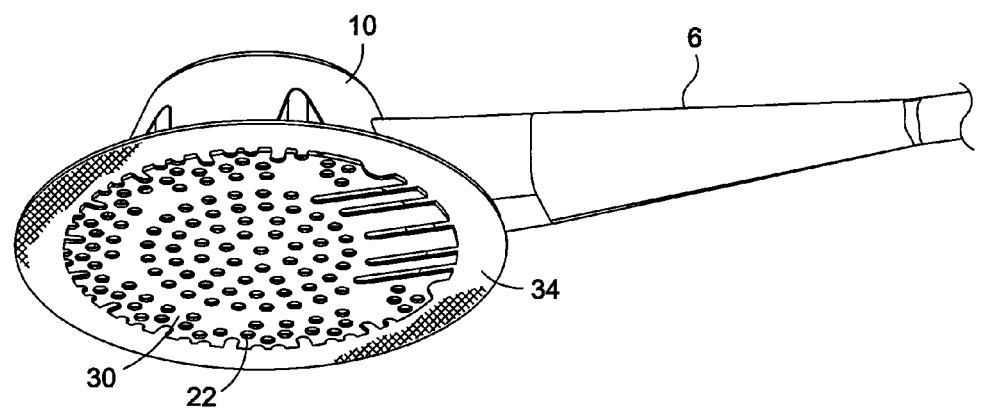
FIG. 3B illustrates a perspective bottom view of a port and the over-molded coupling device of FIG. 3A according to an embodiment of the present invention.

With reference to FIG. 3B, a bottom perspective of an embodiment as illustrated in FIG. 3A is depicted. At least a portion of the coupler 30 comprises through holes 22 to encourage tissue growth. These through holes 22 may be located over a portion of or substantially the entire bottom surface of the coupler 30.

Figure 4:
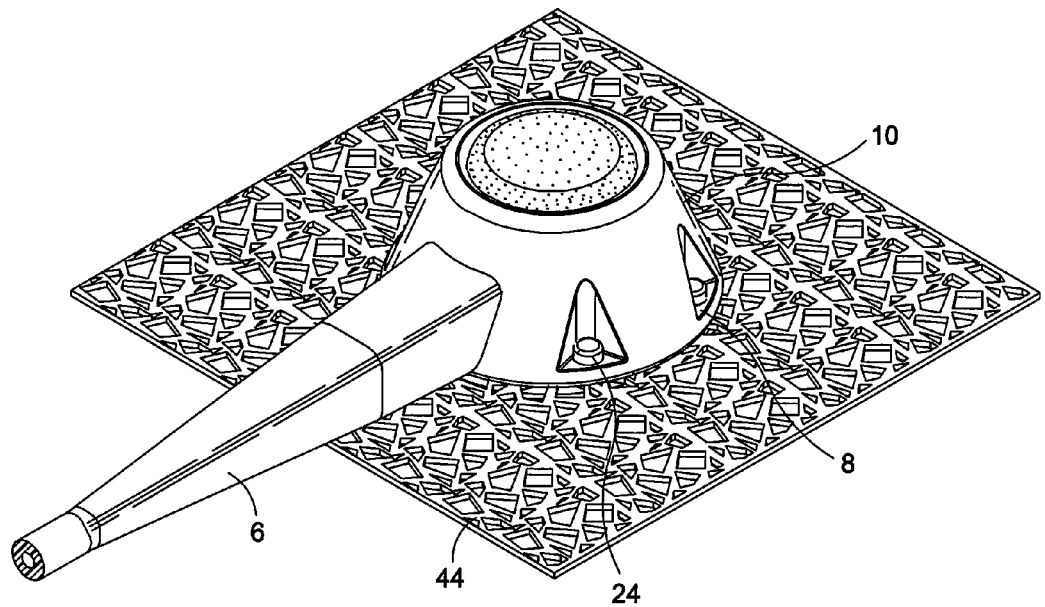
FIG. 4 illustrates a pre-fabricated mesh material coupled to a port according to an embodiment of the present invention.

Turning now to FIG. 4, a pre-fabricated mesh material 44 mated with a port 10 is depicted in accordance with an embodiment. The pre-fabricated mesh material 44 may comprise a mesh made from a polypropylene material that is at least one of pre-cut to desired implantable dimensions or prepared for coupling to a port such as by having openings at predetermined positions for receiving a coupling agent 24. For example, the pre-fabricated mesh material 44 may have a plurality of pre-cut openings through the mesh to receive a coupling agent 24 such as one or more posts configured to create an interference fit with an opening of the anchoring surface 8 of the port 10. In another embodiment, the pre-fabricated mesh material 44 may be made out of any suitable material such as an injection molded plastic or rubber material. The pre-fabricated mesh material 44 properties may be configured to imitate the properties of a traditional mesh and/or organic tissue. In such an embodiment, the pre-fabricated mesh material 44 may be at least one of integral to the housing of the port 10 or comprise a coupling agent 24 on the top surface of the fabricated mesh material 44 to mate with an anchoring surface 8 of the access port 10.

In various embodiments, the pre-fabricated mesh material 44 may be integrally molded into or as part of the base of the access port 10. In such an embodiment, the pre-fabricated mesh material 44 and the base of the access port 10, for example, the bottom surface of the port 10, may be molded as one piece. In addition, the mesh material 44 may be overmolded onto the access port 10, or a portion of the access port 10. The pre-fabricated mesh material 44 and the access port 10 may be made of different materials or the same materials. In one embodiment, the pre-fabricated mesh material 44 may be sandwichably oriented between the access port 10 and a clip 40.

Figure 5:
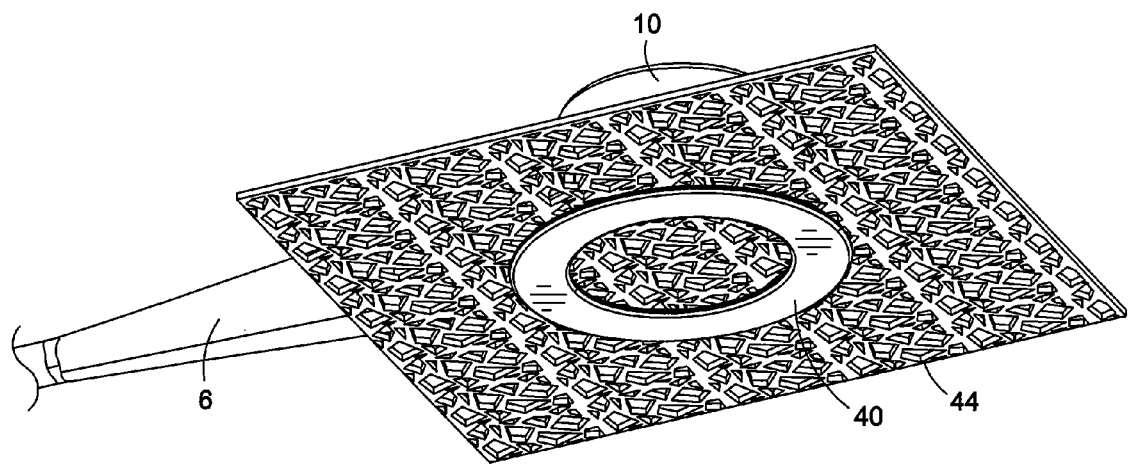
FIG. 5 illustrates a coupling device for retaining a pre-fabricated mesh material to a port according to an embodiment of the present invention.

In accordance with various embodiments, and with reference to FIG. 5, the pre-fabricated mesh material 44 is located between the access port 10 and the clip 40 mated with the access port 10. In other words, the pre-fabricated mesh material 44 may be held in place by the clip 40 positioned on the bottom surface of the pre-fabricated mesh material 44. The coupling agents 24 may be dispersed along the top surface of the clip 40. These coupling agents 24 may be configured for mating with the anchoring surface 8 of the access port 10. Further, in an embodiment, the coupling agents 24 located on the top surface of the clip 40 may be configured to pierce a standard and/or pre-fabricated mesh 44 and then couple with an opening of the anchoring surface 8 of the access port 10 in an interference fit.

The clip 40 may be any suitable size or dimension. In one embodiment, as shown in FIG. 5, the clip 40 may comprise a ring. In other embodiments, the clip 40 may comprise a partial ring and/or other geometric shape. In one embodiment, the clip 40 comprises a single coupling agent 24 configured to pierce a standard and/or pre-fabricated mesh 44 and then couple with an opening of the anchoring surface 8 of the access port 10 in an interference fit. For example, the clip 40 may generally have a tack shape with a base that is larger than the coupling agent 24 post to securely attach a mesh material 44 to an anchoring surface 8 of the access port 10. The clip 40 may be made out of any suitable material such as injection molded plastic or rubber material.

Figure 6:
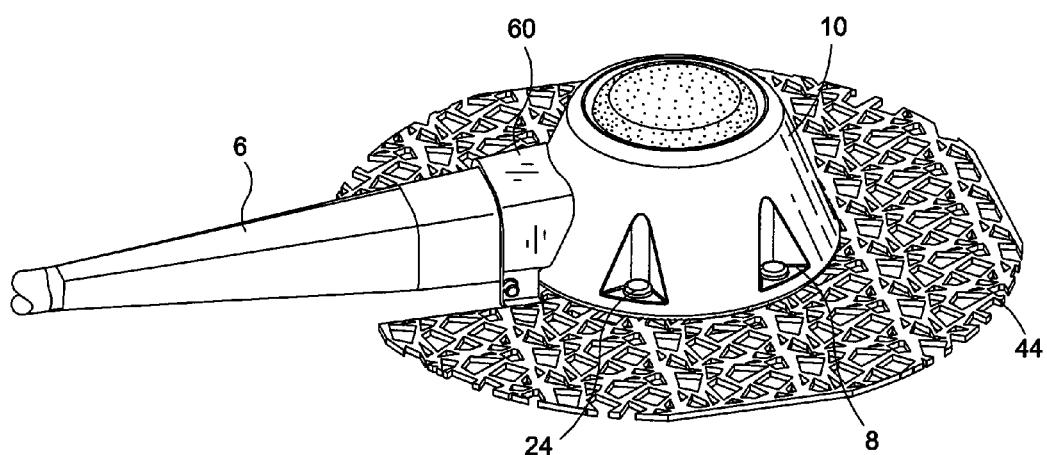
FIG. 6 illustrates a perspective view of a tube shield according to an embodiment of the present invention.

Turning now to FIG. 6, a tube guard 60 is depicted according to various embodiments. The tube guard 60 may be configured to at least partially cover an exterior of the tube 6 that is coupled to the access port 10. The tube guard 60 may be sufficiently robust to protect the tube 6 from errant needle contact or punctures when filling or draining the implantable medical device via a subcutaneous injection through the septum. In one embodiment, the tube guard 60 forming a protective canopy over the tube 6 is anchored to one or more supports coupled to the access port 10, such as supports coupled to the coupler 20 or the pre-fabricated mesh material 44. The tube guard 60 may be hingeably coupled to the coupler 20 or the pre-fabricated mesh material 44. In another embodiment, the tube guard 60 is integral to the access port 10.

In various embodiments, the tube guard 60 is coupled to the pre-fabricated mesh material 44. For example, the pre-fabricated mesh material 44 may be generally shaped with curved outer edges. The pre-fabricated mesh material 44 may comprise a notch under the tube 6 to allow the tube 6 to travel and flex through a plane parallel to the bottom surface of the pre-fabricated mesh material 44 without interference from the pre-fabricated mesh material 44.

In one embodiment, the side(s) of the tube guard 60 adjacent to the port 10 is configured to mirror the side surface properties of the access port 10 to reduce the chance of errant needle punctures in the protected tube 6. The tube guard 60 may extend from the access port 10 over the tube 6 in any desired dimension for any desired length. As the distance of the tube 6 from the top surface of the access port 10 increases, the likelihood of a puncture by a needle decrease and the need for the tube guard 60 coverage decreases.

In some embodiments, the tube 6 may be protected by additional shields such as a plurality of individual shields, or beads, coupled to the tube 6 and spaced adjacent to one another. Each individual shield may be configured to have a generally cylindrical shape that wraps around or partially around an outer circumference of a portion of the tube 6. Additional details regarding exemplary tube shields and puncture resistant configurations are disclosed in co-pending U.S. patent application Ser. No. 12/771,609 filed on Apr. 30, 2010 and entitled "IMPLANTABLE DEVICE TO PROTECT TUBING FROM PUNCTURE" having common ownership as the present application, the contents of which are hereby incorporated by reference in their entirety.

Figure 7:
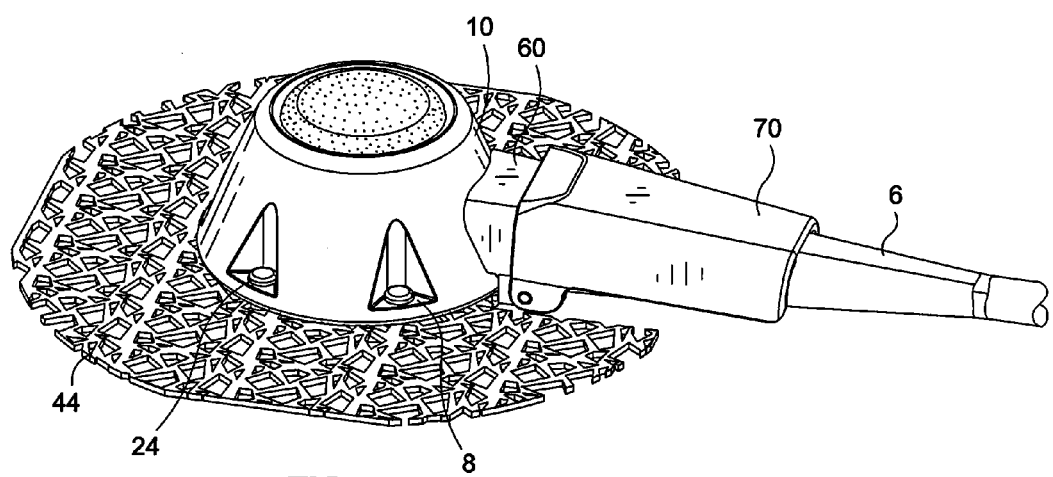
FIG. 7 illustrates a perspective view of an extended tube shield and a hinged link according to an embodiment of the present invention.

As depicted in FIG. 7, the tube guard 60 may comprise one or more pivoting link element 70 to both increase the length of the tube 6 that is protected and allow for the tube 6 to travel in one or more directions without interference. These pivoting link elements 70 may be made from the same or similar materials as the tube guard 60 and/or the access port 10. This pivoting link element 70 may be attached on a pivoting hinge to at least one of the access port 10, the tube guard 60, an additional pivoting link 70, or the coupler 20. The pivoting link 70 may extend distally from the tube guard 60. Also, though depicted with the pivoting link 70 on top of a portion of the tube guard 60 in FIG. 7, it is understood that the pivoting link 70 may be nested underneath a portion of the tube guard 60, or under the additional pivoting link 70 (for example, as illustrated in FIGS. 8A and 8B).

Figure 8A:
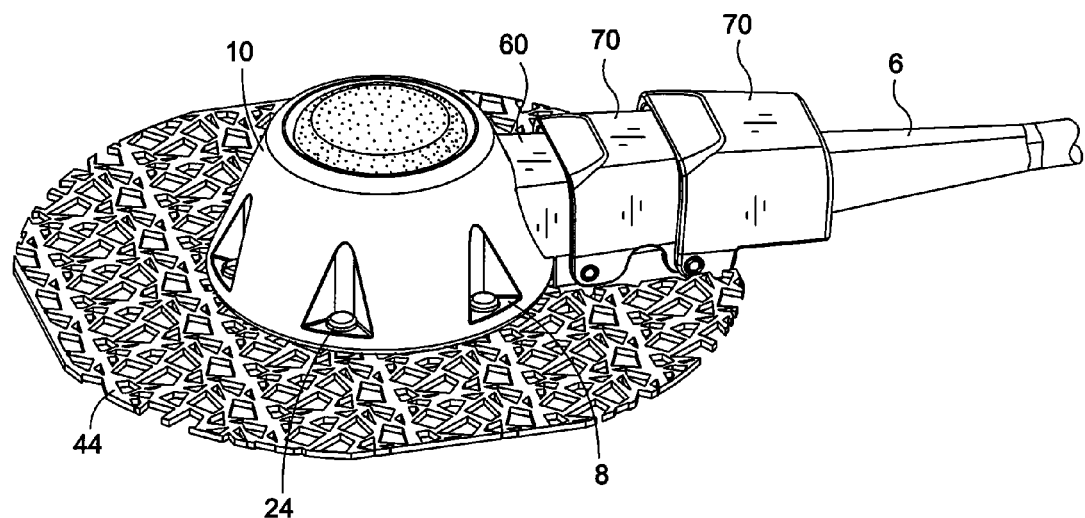
FIG. 8A illustrates a perspective view of an extended tube shield and two hinged links according to an embodiment of the present invention.
Figure 8B:
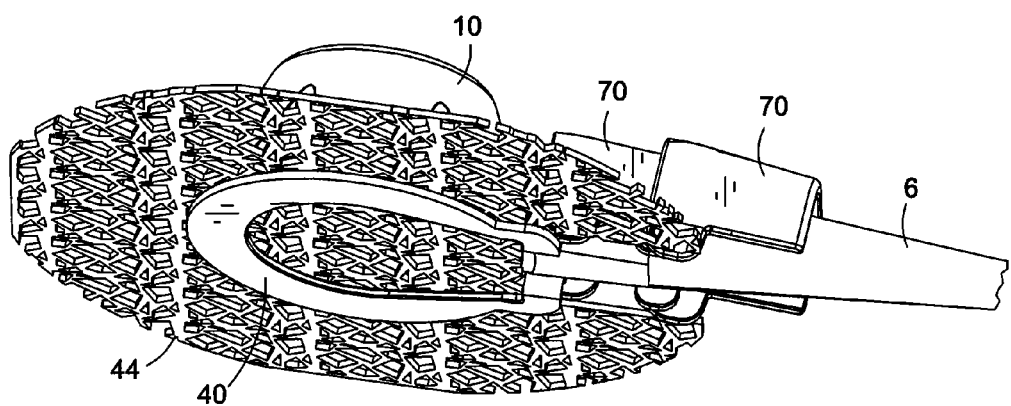
FIG. 8B illustrates a perspective bottom view of the extended tube shield and the hinged link of FIG. 8A according to an embodiment of the present invention.

Turning now to FIGS. 8A and 8B, the tube guard 60 with multiple pivoting link elements 70 coupled to a clip 40 is illustrated in accordance with various embodiments. The prefabricated mesh material 44 may be configured to receive one or more coupling agents 24 through pre-determined openings in the pre-fabricated mesh material 44. The pre-fabricated mesh material 44 may be positioned in between the top surface of the clip 40 and the bottom surface of the access port 10. The prefabricated mesh material 44 has a notch under the tube 6 exiting the side wall of the port 10 to allow the tube 6 to flex in the downward direction without interference from the pre-fabricated mesh material 44. The clip 40 generally forms a partial ring to similarly allow the tube 6 to flex in the downward direction without interference from the clip 40.

Figure 9A:
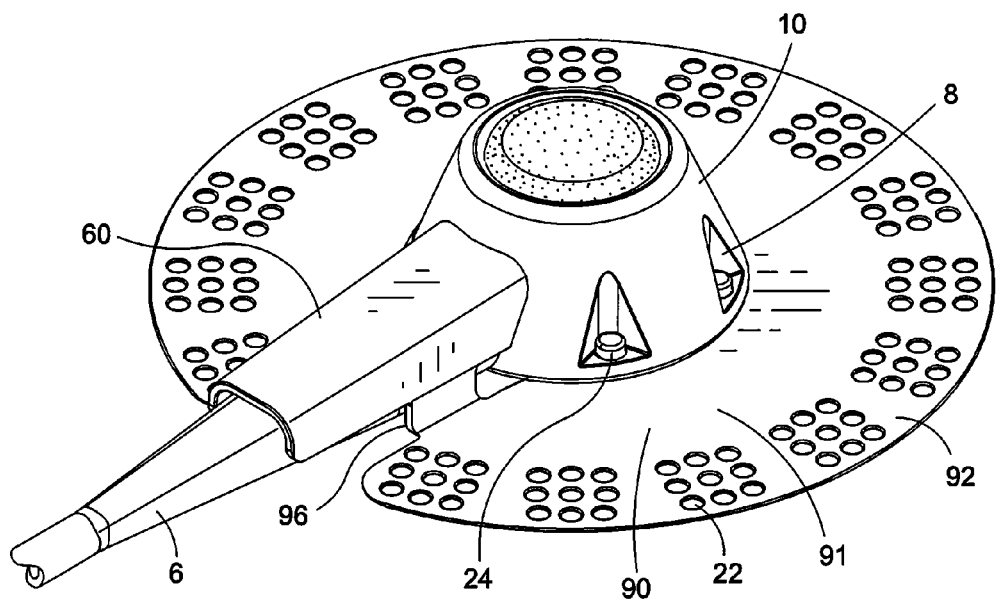
FIG. 9A illustrates a perspective view of a tissue shield according to an embodiment of the present invention.
Figure 9B:
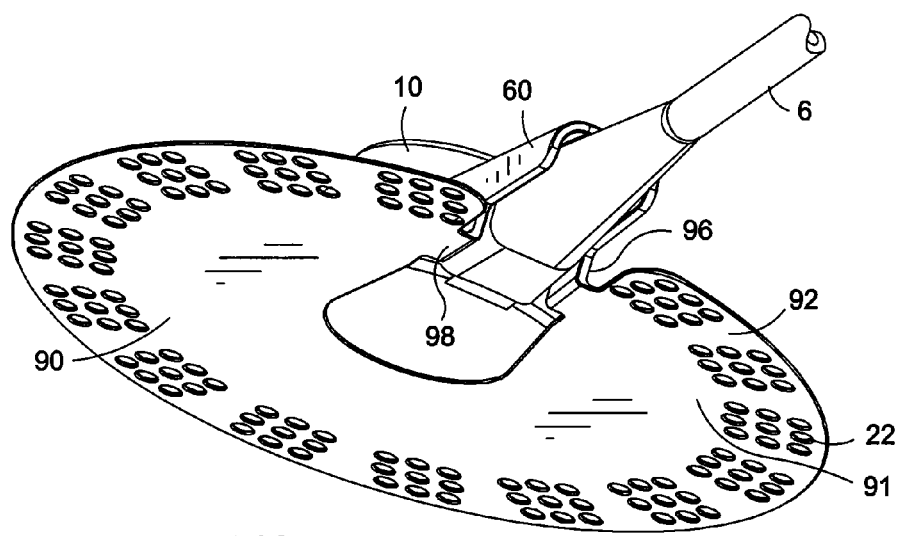
FIG. 9B illustrates a perspective bottom view of the tissue shield of FIG. 9A according to an embodiment of the present invention.

Further, in accordance with various embodiments, FIGS. 9A and 9B illustrate a perspective view of the coupler 20 having a tissue shield 90 and the tube guard 60. For example, the coupler 20 may comprise a first portion 91 without through holes 22 and a second portion 92 having through holes 22. The first portion 91 without through holes may act as a tissue guard protecting the surface underneath the first portion 91 from contact with the needle. The likelihood of errant needle sticks/strikes is proportional to the distance from the access port 10. Stated another way, as the distance away from the access port 10 increases, the likelihood of errant needle strikes decreases. Thus, in one embodiment, the second portion 92 comprising though holes 22 is located towards the exterior perimeter of the coupler 20 and the first portion 91 without the through holes 22 is located near the access port 10. In this embodiment, though it may be any suitable length, the tube guard 60 extends from the access port 10 to the outer perimeter of the coupler 20.

In one embodiment, the coupler 20 comprises at least one coupling agent 24 configured to mate with an anchoring surface 8 of the access port 10 such as an existing suture hole of the access port 10 via an interference fit. The tube guard 60 is coupled to the coupler 20 via a plurality of attachment tabs 96 and 98. These attachment tabs 96, 98 may be any suitable shape and width. For example, the width of the attachment tabs 96 and 98 may run substantially the entire length of the tube shield 60, or the widths of the attachment tabs 96 and 98 may comprise a portion of the width of tube shield 60 (as shown). The attachment tabs 96 and 98 may have equal widths or unequal widths. Moreover, there may be fewer or more attachment tabs 96 and 98 as desired. In one embodiment, the attachment tabs 96 and 98 are configured to flex. Further, in an embodiment, the coupler 20 of FIGS. 9A and 9B may include one or more flanges 26 and/or one or more pivoting links 70 as desired.

Figure 10A:
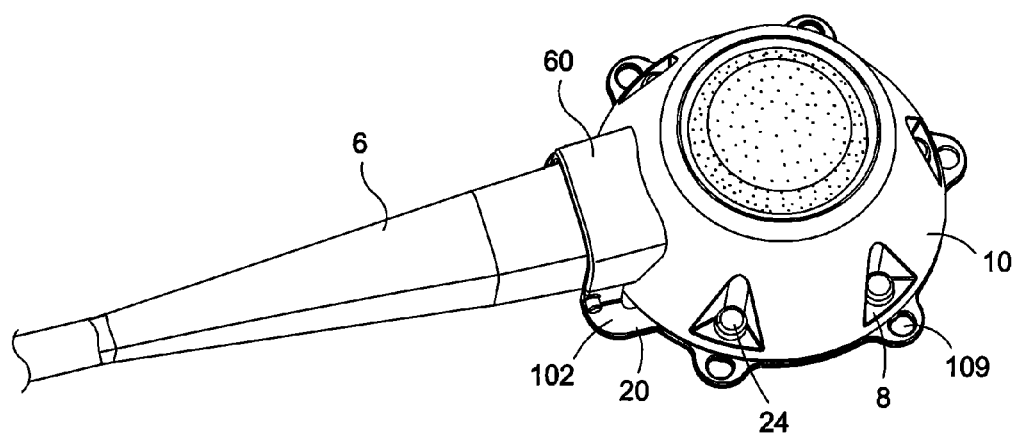
FIGS. 10A and 10B illustrate perspective views of a tube shield according to an embodiment of the present invention.
Figure 10B:
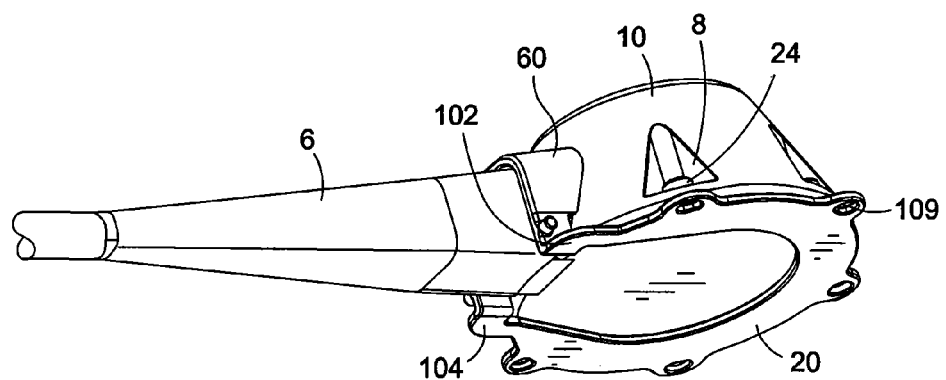

FIGS. 10A and 10B illustrate perspective view of the coupler 20 and the tube guard 60 in accordance with further embodiments. For example, the coupler 20 comprises at least one coupling agent 24 configured to mate with the anchoring surface 8 of the access port 10, such as with an existing suture hole of the access port 10 via an interference fit. The tube guard 60 may be integral to the coupler 20 or the tube guard 60 may be coupled to the coupler 20 via a plurality of attachment tabs 102 and 104. These attachment tabs 102, 104 may be any suitable shape and width. The coupler 20 may mate with one or more anchoring surfaces 8 of the access port 10 via one or more coupling agents 24. Stated another way, the coupler 20 may mate with any available anchoring surface 8, such as with any available suture hole or holes of the port 10, leaving three or more open suture holes to suture the access port 10 to a patient.

In an embodiment, the coupler 20 may replicate the exiting anchoring surfaces 8 used by the coupling agents 24 adjacent to the anchoring surfaces 8. These replicated anchoring surfaces 109 may be coupled to tissue, mesh, a second coupler, additional coupling agents 24, or the pre-fabricated mesh material 44 as desired. In one embodiment, the coupler 20 of FIGS. 10A and 10B may include a tissue shield as previously disclosed, and/or one or more pivoting links 70 as desired.

Figure 11A:
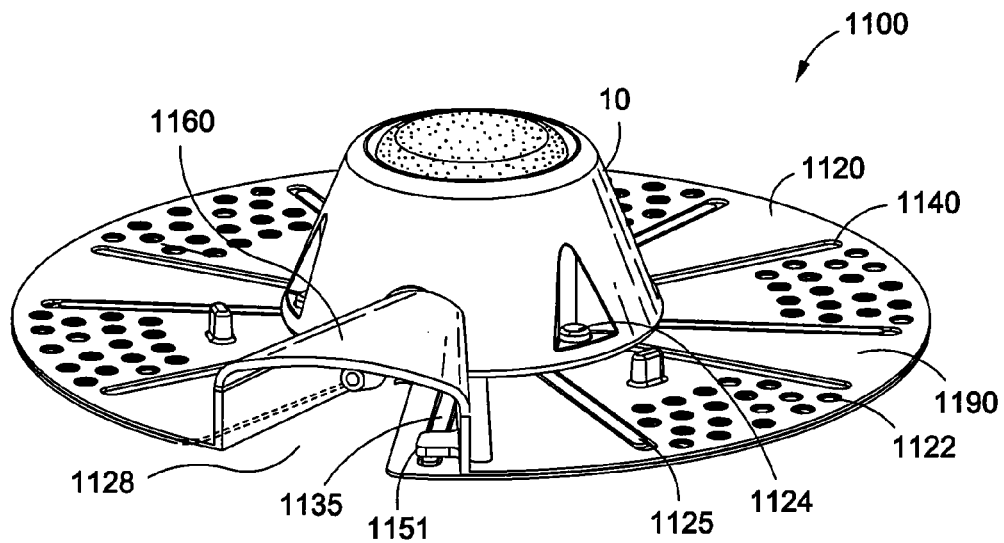
FIG. 11A illustrates a perspective view of a tube and a tissue shield anchoring device according to an embodiment of the present invention.
Figure 11B:
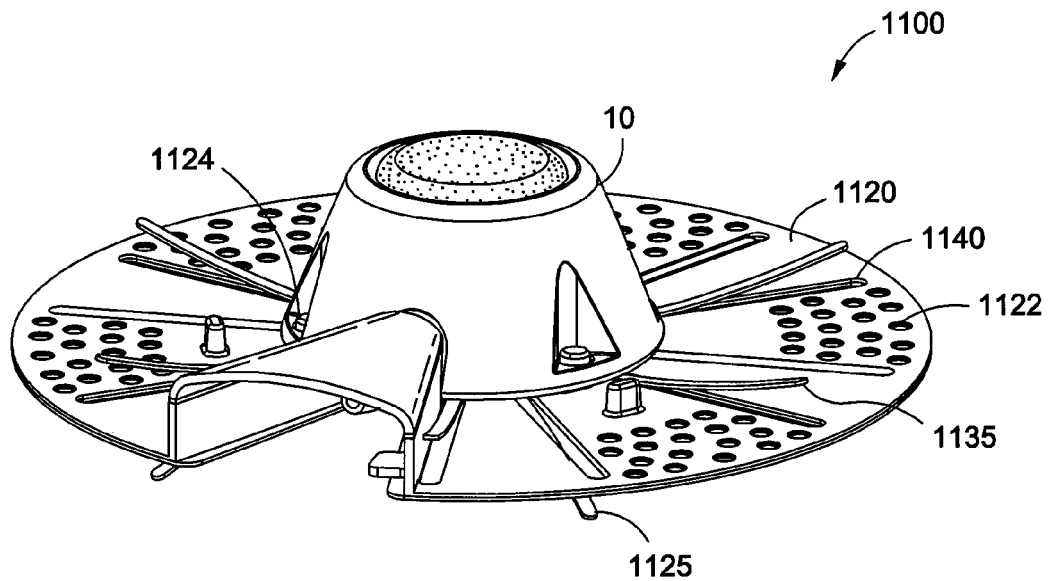
FIG. 11B illustrates a perspective view of a deployed tube and a tissue shield anchoring device according to an embodiment of the present invention.
Figure 11C:
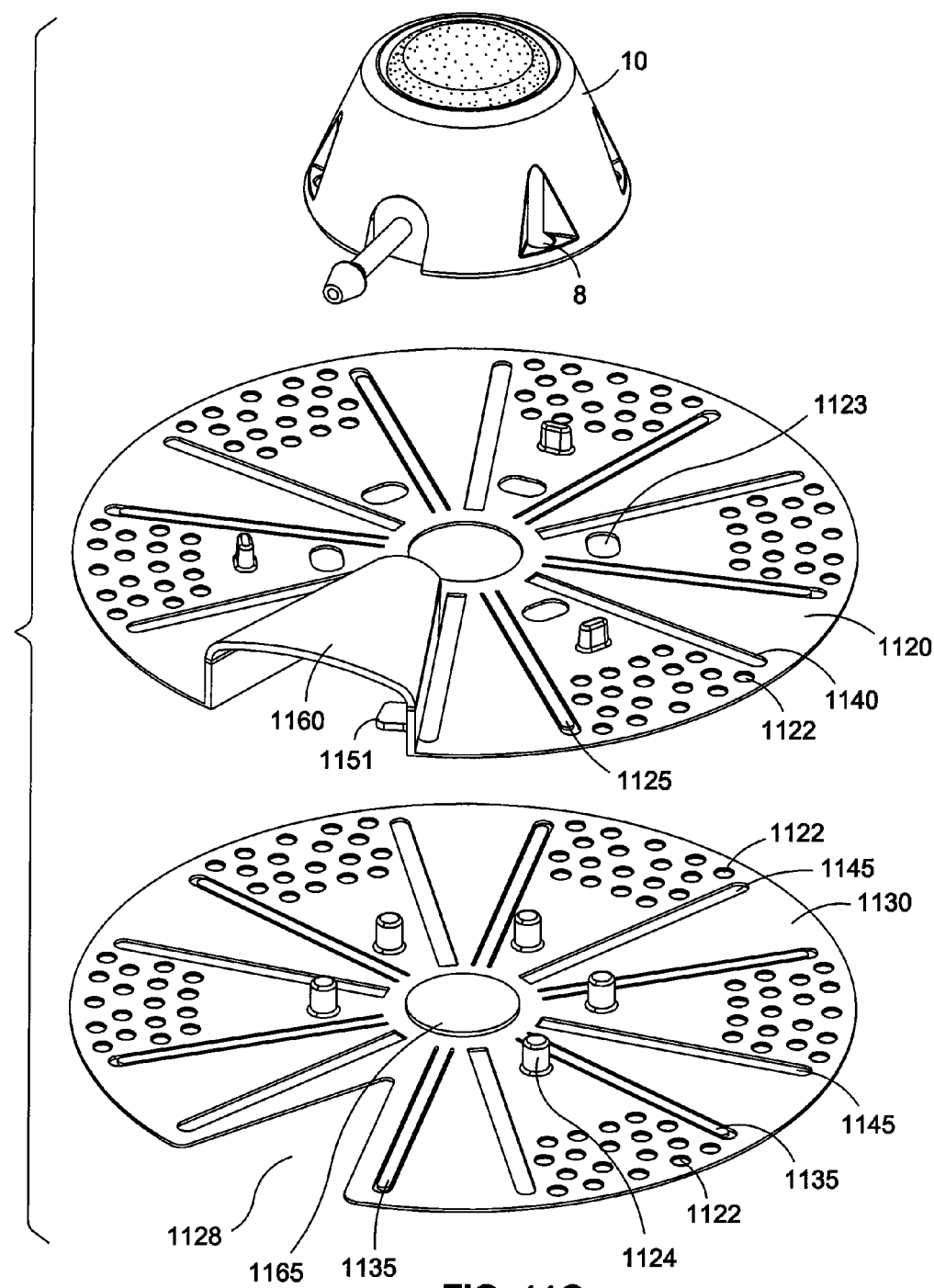
FIG. 11C illustrates an exploded view of the tube and the tissue shield anchoring device of FIGS. 11A and 11B according to an embodiment of the present invention.

FIGS. 11A-11C illustrate perspective views of an anchoring device 1100 according to an embodiment of the present invention. The anchoring device 1100 comprises a tissue shield 1190, a tube guard 1160, at least one through hole 1122, and at least one anchoring beam 1125, 1135. The anchoring device 1100 comprises a first element 1120 and a second element 1130.

The first element 1120 comprises a top surface and a bottom surface. The first element 1120 comprises through holes 1122 passing from the bottom surface to the top surface through the first element 1120. Coupled to the top surface and/or side surface of the first element 1120 is a tube guard 1160. The tube guard 1160 forms a canopy protecting at least a portion of a tube 6 configured to be coupled to the port 10. This tube guard 1160 is configured to protect the tube 6 from unintended needle contact. The tube guard 1160 may be any suitable shape and dimension. Similar to previously described tube guards, the side surface adjacent to the port 10 of the tube guard 1160 may be shaped to mirror the side surface of the port 10. A side interior wall of the tube guard 1160 may comprise a tab 1151 for depressing an anchor beam 1135 while the first element 1120 is in a first position described in further detail below.

The top surface of the first element 1120 also comprises openings 1123 for receiving the coupling agents 1124. The first element 1120 also comprises at least one anchoring beam 1125 that is notched out of the first element 1120 and pre-bent so that at rest the orientation of the anchoring beam 1125 is in a deployment position. For example, a deployment position may extend out from the respective first element 1120 and the second element 1130 at an angle configured to interact with surrounding tissue and internal bodies of the patient. The anchor beams 1125 and 1135 in a deployment position may be configured to orient anchoring device 1100 in a selected orientation and position. The first element 1120 further comprises at least one opening 1140 for receiving at least one anchoring beam 1135 from the second element 1130.

The second element 1130 comprises a top surface and a bottom surface. The second element 1130 comprises through holes 1122 passing from the bottom surface to the top surface through second element 1130. The top surface of the second element 1130 also comprises the coupling agents 1124 for mating with an anchoring surface 8 of the access port 10, similar to the previously described coupling agents 24. The second element 1130 further comprises at least one opening 1145 for receiving at least one anchoring beam 1125 from the first element 1120. The second element 1130 comprises a notch 1128 under the tube 6 to allow the tube 6 to travel and flex through a plane parallel to the bottom surface of the second element 1130 without interference from the anchoring device 1100. The second element 1130 further comprises a ridge 1165 with a height greater than the thickness of the first element 1120. The ridge 1165 allows the first element 1120 to rotate about an axis while the first element 1120 is coupled between the second element 1130 and the access port 10. The second element 1130 also comprises at least one beam 1135 that is notched out of the second element 1130 and pre-bent so that at rest the preferred orientation of the beam 1135 is in a deployed position.

In one embodiment, the elements of the anchoring device 1100 may be coated with a bioresorbable material, for example, to encourage biological compatibility between the anchoring device 1100 and the body tissue. The coating may cover the entirety of the anchoring device 1100 or only a portion of the anchoring device 1100. A thickness of the coating may be even, or may vary along the surface of the anchoring device 1100. The coating may be deposited through a process including a spraying process, dipping process, molding process, wiping process, or other equivalent means of attaching the bioresorbable material to the anchoring device 1100. The coating thickness may vary between approximately 0.001 inches and 0.25 inches. The bioresorbable material serves to form a biological seal between the access port 10 and the body tissue, and to encourage compatibility between the access port 10 and the body tissue.

As illustrated in FIGS. 11A-11C, in accordance with various embodiments, the first element 1120 is coupled between the access port 10 and the second element 1130, for example, in a sandwich configuration or orientation. The coupling agents 1124 of the second element 1130 pass up through openings in first element 1120 and mate with an anchoring surface 8 such as a suture hole of the access port 10. The anchoring device 1100 is initially set in a first position with anchoring beams 1125 and 1135 flush with the first element 1120 and the second element 1130 during implantation. The first element 1120 is then rotated a pre-selected number of degrees to a second position and one or more of the anchoring beams 1125 pass down through a respective opening in the second element 1130 to a deployed position. Similarly, one or more of the anchoring beams 1135 pass up through a respective opening in the first element 1120 to a deployed position. Once the anchoring device 1100 is placed into the second position with the anchoring beams 1125 and 1135 deployed, the anchoring device 1100 may not be returned to the first position.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable coupling device configured to facilitate coupling an implantable access port to a tissue of a patient, the implantable coupling device comprising:
    a porous coupling member having a top surface and a bottom surface; and
    a coupling agent proximate the top surface of the porous coupling member for mating with a base of the implantable access port of an adjustable gastric banding system,
    wherein the porous coupling member extends substantially parallel to the base of the implantable access port,
    wherein the bottom surface of the porous coupling member is configured for anchoring the porous coupling member to the tissue of the patient, and
    wherein the porous coupling member comprises a raised canopy configured to permit a tube coupled to a side surface of the implantable access port to pass through the raised canopy, and wherein a surface of the raised canopy is configured to shield the tube from contact with a needle.

2. The implantable coupling device of claim 1, wherein the porous coupling member is made from injection moldable plastic or rubber.

3. The implantable coupling device of claim 1, further comprising a flange coupled to the porous coupling member.

4. The implantable coupling device of claim 1, wherein the porous coupling member is over-molded on at least one of a fabric or woven mesh material.

5. The implantable coupling device of claim 1, further comprising:
   a first portion of the porous coupling member extending substantially parallel to the base of the implantable access port, wherein the first portion does not comprise a porous surface; and
   a second portion of the porous coupling member extending substantially parallel to the base of the implantable access port, wherein the second portion comprises a porous surface, and wherein the first portion includes the surface of the raised canopy configured to shield a portion of the patient from contact with the needle.

6. The implantable coupling device of claim 5, wherein the first portion is proximate to the implantable access port.

7. The implantable coupling device of claim 1, wherein a surface of the raised canopy is formed to substantially mirror a portion of the side surface of the implantable access port.

8. The implantable coupling device of claim 1, wherein the raised canopy is integral to the porous coupling member.

9. The implantable coupling device of claim 1, wherein the raised canopy is hingeably coupled to the porous coupling member.

10. The implantable coupling device of claim 1, wherein the porous coupling member further comprises a notch under the raised canopy configured to permit the tube to flex below the plane of the bottom surface of the porous coupling member without interference with the porous coupling member.

11. An implantable coupling device configured to facilitate coupling an implantable access port to a tissue of a patient, the implantable coupling device comprising:
   a porous coupling member having a top surface, a bottom surface, a raised canopy configured to permit a tube coupled to a side surface of the implantable access port to pass through the raised canopy, and a hingeable shroud extending distally from the canopy; and
   a coupling agent proximate the top surface of the porous coupling member for mating with a base of the implantable access port of an adjustable gastric banding system,
   wherein the porous coupling member extends substantially parallel to the base of the implantable access port,
   wherein the bottom surface of the porous coupling member is configured for anchoring the porous coupling member to the tissue of the patient.

12. An implantable coupling device, comprising:
   a coupling member having a top surface and a bottom surface;
   a coupler proximate the top surface, wherein the coupler is configured to mate with the base of an implantable access port of an adjustable gastric banding system;
   a mesh material oriented between the implantable access port and the coupling member; and
   a through hole in the mesh material configured to allow the coupler to pass through the through hole to mate with the base of the implantable access port.

13. The implantable coupling device of claim 12, wherein the mesh material is a pre-fabricated mesh material made from injection moldable plastic or rubber.

14. The implantable coupling device of claim 12, wherein the coupling member further comprises a raised canopy configured to permit the passage of a tube coupled to a side surface of the implantable access port.

15. The implantable coupling device of claim 12, wherein the coupling member further comprises a flange configured to flex with the movement of the tissue of the patient.

16. The implantable coupling device of claim 12 wherein the coupler is at least one of a partial ring shape or a substantially circular shape.

17. An implantable coupling device configured to facilitate coupling an implantable access port to a tissue of a patient, the implantable coupling device comprising:
   a coupling member having a top surface and a bottom surface, wherein the coupling member further comprises a raised canopy configured to permit the passage of a tube coupled to a side surface of the implantable access port and to provide shielding of the tube, wherein coupling member is configured for anchoring the coupling member to a tissue of a patient; and
   a coupling agent proximate the top surface of the porous coupling member for mating with a base of the implantable access port of an adjustable gastric banding system.

18. An implantable anchoring device comprising:
   a first anchoring member and a second anchoring member, the first anchoring member comprising:
      a first top surface and a first bottom surface; and
      a first beam configured to extend through a first opening in the second anchoring member in response to the first anchoring member being rotated about an axis from a first position to a second position;
   wherein the second anchoring member comprises:
      a second top surface and a second bottom surface; and
      a second beam configured to release through a second opening in the first anchoring member in response to the first anchoring member being rotated about the axis from the first position to the second position, wherein the second top surface of the second anchoring member is configured to attachably mate with a base of an implantable access port housing of an adjustable gastric banding system.

19. The implantable coupling device of claim 18, wherein the first beam is integral to the first anchoring member and wherein the second beam is integral to the second anchoring member.

20. The implantable coupling device of claim 18, wherein the first beam and the second beam are configured to return to a preset deployed position in response to the first anchoring member being moved from the first position into the second position.

* * * * *